United States Patent [19]

Connor et al.

[11] 3,983,237
[45] Sept. 28, 1976

[54] 2-ARYL SUBSTITUTED ISOXAZOLO[2,3-a]PYRIDINYL HALIDES

[75] Inventors: David T. Connor, Parsippany;
Patricia A. Young, Madison;
Maximilian von Strandtmann,
Rockaway Township, all of N.J.

[73] Assignee: Warner-Lambert Company, Morris Plains, N.J.

[22] Filed: Sept. 8, 1975

[21] Appl. No.: 611,281

[52] U.S. Cl. .............................. 424/263; 260/297 B
[51] Int. Cl.² ........................................ A61K 31/44
[58] Field of Search ................. 260/297 B; 424/263

[56] References Cited
OTHER PUBLICATIONS
Chemical Abstracts 8th Collective Index, (1971), p. 168355.
Chemical Abstracts 7th Collective Index, (1966), p. 12,447S.

*Primary Examiner*—Norman A. Drezin
*Attorney, Agent, or Firm*—Albert H. Graddis; Frank S. Chow; Anne M. Kelly

[57] ABSTRACT

2-Aryl substituted isoxazolo[2,3-a]pyridinyl halides having the formula I:

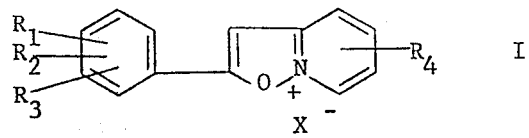

wherein $R_1$, $R_2$ and $R_3$ are each hydrogen, halogen, hydroxy, lower alkyl, lower alkoxy or lower alkanoyl; $R_4$ is hydrogen or lower alkyl; X is a bromide, chloride or iodide salt; and processes for the preparation thereof, are described. The compounds of the invention are useful as anti-inflammatory agents and for the treatment of hyperacidity.

20 Claims, No Drawings

2-ARYL SUBSTITUTED ISOXAZOLO[2,3,-a]PYRIDINYL HALIDES

DESCRIPTION OF THE PRIOR ART

Osborne et al., in J. Heterocyclic Chem., 1: 138–140 (1964), describe the preparation of 1-phenyl-2-(2-pyridinyl)ethanone N-oxide by the acylation of 2-picoline N-oxide, using sodium amide in liquid ammonia as the condensing agent. No pharmacological activity is reported for this or related compounds described by Osborne et al.

DESCRIPTION OF THE PARTICULAR EMBODIMENTS

This invention relates to 2-aryl substituted isoxazolo[2,3-a]pyridinyl halides having the formula I:

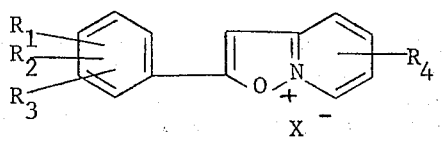

wherein $R_1$, $R_2$ and $R_3$ are each hydrogen, halogen, hydroxy, lower alkyl, lower alkoxy or lower alkanoyl; $R_4$ is hydrogen or lower alkyl; X is a bromide, chloride or iodide salt. Compounds of the formula I above, wherein $R_1$ is hydrogen, halogen, hydroxy, methyl, methoxy or acetoxy; $R_2$ is hydrogen, hydroxy, methyl, methoxy or acetoxy; $R_3$ is hydrogen or hydroxy; $R_4$ is hydrogen or methyl; and X is the bromide salt.

The compounds of the formula II:

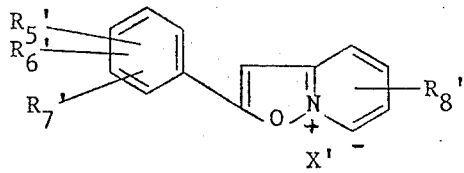

wherein $R_5'$, $R_6'$ and $R_7'$ are each hydrogen, halogen, hydroxy, lower alkyl or lower alkoxy; $R_8'$ is hydrogen or lower alkyl; and X' is a bromide, chloride or iodide salt, are prepared by treating a compound of the formula III:

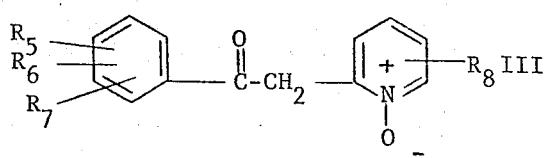

wherein $R_5$, $R_6$ and $R_7$ are each hydrogen, halogen, hydroxy, lower alkyl or lower alkoxy and $R_8$ is hydrogen or lower alkyl, with a hydrohalide acid and a lower alkanoic acid to effect ring closure. In the course of this reaction, one or more lower alkoxy substituents on compound III is converted into a hydroxy substituent on final compound II unless certain other protective substituents are present in specific positions. Thus, it appears that a protective effect is exerted by a halogen group, positioned para to the lower alkoxy group on the phenyl ring of compound III. Additionally, the same protective effect is exerted by a lower alkyl group, positioned ortho to the N-oxide (that is, when $R_8$ is lower alkyl, ortho to the N-oxide) when a lower alkoxy is, at the same time, positioned ortho to the carbonyl group on compound III starting material. In either of the above two instances, the lower alkoxy radical on compound III does not undergo conversion to a hydroxyl group.

A final compound II containing one or more hydroxyl substituents may be subjected to standard alkylation procedures in order to obtain the corresponding lower alkoxy substituents, if desired. Typically, such procedures involve the use of a dialkyl sulfate in the presence of base, such as sodium hydroxide; or the use of an alkyl iodide in the presence of a base, i.e, potassium carbonate. For methylation reactions, diazomethane may be used.

A final compound II containing one or more alkanoyl substituents may be obtained by subjecting the corresponding hydroxy substituted final compound to treatment with a lower alkanoic acid anhydride to convert hydroxyl substituents to lower alkanoyl substituents.

Compound III starting materials used in preparing the compounds of this invention are obtained as described in U.S. Ser. No. 611,282, filed Sept. 8, 1975. Thus, the compound III starting materials may be generally prepared by reacting a substituted benzoic acid ester with a substituted 2-picoline N-oxide in liquid ammonia in the presence of an alkali amide condensing agent. Typically, a sodium, potassium or lithium amide is used as the condensing agent. If one or more hydroxyl substituents are desired on the compound III, it is necessary to react a benzyloxy substituted benzoic acid with the 2-picoline N-oxide, using the same reaction conditions, and then subject the intermediate obtained to catalytic reduction (gaseous hydrogen and a palladium-on-carbon catalyst) to reduce the benzyloxy substituents present on the intermediate to the desired corresponding hydroxy groups.

Representative compound III starting materials which may be prepared by the above-described reactions include: 1-(3-chloro-4-hydroxyphenyl)-2-(2-pyridinyl)ethanone N-oxide, 1-(4-bromo-3,5-dihydroxyphenyl)-2-(2-pyridinyl)-ethanone N-oxide, 1-(5-bromo-2-chlorophenyl)-2-(2-pyridinyl)-ethanone N-oxide, 1-(3,5-diiodo-2-hydroxyphenyl)-2-(2-pyridinyl)ethanone N-oxide, 1-(5-bromo-2-chlorophenyl)-2-(6-methyl-2-pyridinyl)ethanone N-oxide, 1-(2,6-dimethoxyphenyl)-2-(2-pyridinyl)ethanone N-oxide, 1-(3-fluoro-4-methylphenyl)-2-(2-pyridinyl)ethanone N-oxide, 1-(3-hydroxy-4-methylphenyl)-2-(2-pyridinyl)ethanone N-oxide, 1-(3,4,5-triiodophenyl)-2-(2-pyridinyl)ethanone' N-oxide, 1-(3-fluoro-4-methylphenyl)-2-(6-methyl-2-pyridinyl)-ethanone N-oxide, and 1-(3-hydroxy-4-methylphenyl)-2-(6-methyl-2-pyridinyl)ethanone N-oxide.

In the above formulas for the compounds of the invention, the R group definition may be more fully described as follows: the term "lower alkyl" is meant to include lower aliphatic hydrocarbons having from 1 to 7 carbon atoms, preferably 1 to 4 carbon atoms in the alkyl chain, such as methyl, ethyl, propyl, isopropyl, butyl, isobutyl and the like. This definition for lower alkyl also applies to the alkyl portions of the alkoxy, alkanoyl and alkanoic terms. The term "halogen" is meant to include bromine, chlorine, iodine and fluorine. The term "halide" is meant to include bromide, chloride and iodide.

The compounds of this invention having the formula I exhibit gastric anti-secretory activity when tested according to the procedures described by H. Shay et al., Gastroenterology, 5: 43 (1954). In this last-mentioned test, male Long Evans Hooded rats (150–200 gms.) are fasted for 24 hours prior to testing (water ad lib). Rats are randomly divided into groups of 5 rats each and housed individually. At the time of testing, each rat is lightly anesthetised with ether, its stomach exposed through a midline abdominal incision and the pylorus ligated with silk thread. The incision is sutured, closed and covered with Flexible Collodion, U.S.P. to prevent ingestion of blood. Test compound or vehicle control is administered (a) intraduodenally prior to closing the incision; (b) intraperitoneally immediately after ligation; or (c) orally as a one hour pretreatment. Four hours later, the rats are sacrificed by ether and their stomachs removed and opened.

Gastric contents are placed in centrifuge tubes and centrifuged to remove debree. The volume of gastric juice is measured (expressed in milliliters) and titratable acidity determined electrometrically to pH 7.4 (expressed as milliequivalents of acid per liter). Results are expressed as percent reduction of volume and/or titratable acidity from control group average. Reduced gastric acid secretion in experimental animals in the above-described test is considered to be repesentative of pharmacological utility in the treatment of hyperacidity in humans.

Thus, the compounds of the invention are active in the treatment of hyperacidic conditions when administered to mammals at a dose level of from about 5 to about 20 mg/kg of body weight by the oral or parenteral route. This dosage may be varied depending on the severity of the condition, the age, weight, sex and class of mammal being treated as well as the route of administration. For example, when 2-(2-hydroxy-5-methylphenyl)isoxazolo[2,3-a]pyridinium bromide (the compound of Example 4) is tested in the pylorus ligated rat in the above-described procedure, at a dose of about 20 mg/kg, intraperitoneally, a reduction of 66.3% in the volume of gastric acid and a reduction of 9.3% in the ion acid is obtained, compared to controls. Similarly, in this same test, 2-(2-methoxyphenyl)-7-methylisoxazolo[2,3-a]pyridinium bromide (the compound of Example 7) caused a reduction of 81.6% in the volume of gastric acid, compared to controls.

In addition to the pharmaceutical activity, the compounds of the invention are also useful as anti-inflammatory agents, as evidenced by results obtained in the carragennin-induced rat paw edema test. In this last-mentioned test, intact or adrenalectromized male albino rats (S-D) derived) weighing 150–170 g. are arranged in groups of 10–15. The adrenalectromized rats, which are used one week after operation, are maintained with either 0.9% saline or hydrocortisone acetate (0.1 mg/animal). One hour after the administration of the test compounds (orally or parenterally), 0.05 ml of 1% carrageenin suspension is injected into the plantar area of the left hind paw. Three hours later, the difference between the left and right hind paws, which is measured by the displacement of mercury, is recorded. Results are expressed as percent change from the controls. The test is described in Arch. Internat. Pharmacodynam. Therap., 203: No. 1, 92 100, May 1973 by D. Pasquale, et al., and in the earlier work by Winter et al., Proc. Soc. Exp. Biol. N.Y., 111: 544, 1962.

Reduced inflammation in experimental animals in the above-described test is considered to be representative of pharmaceutical activity in the conditions where the soft tissues are inflamed, such as rheumatiod arthritis.

Thus, the compounds of the invention are active in the treatment of inflammatory conditions when administered to mammals at a dose level of from about 50 to about 100 mg/kg of body weight by the oral route. This dosage may be varied depending on the severity of the condition, the age, weight, sex and class of mammals being treated, as well as the route of administration. For example, when 2-(2-methoxyphenyl)-7-methylisoxazolo[2,3-a]pyridinium bromide (the compound of Example 7) is tested in the carrageenin-induced rat paw edema test, at a dose of about 100 mg/kg, administered orally, a reduction of 40% in the amount of inflammation was obtained, compared to controls.

In use, the compound of the invention may be combined with pharmaceutically acceptable vehicles such as gum tragacanth in saline suspension to provide dosage forms for parenteral administration; or they may be combined with pharmaceutical diluents such as lactose, cornstarch, and the like and formulated into tablet or capsule dosage forms.

To further illustrate the practice of this invention, the following examples are included:

EXAMPLE 1

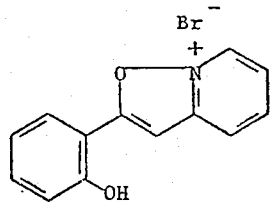

2-(2-Hydroxyphenyl)Isoxazolo[2,3-a]Pyridinium Bromide 1-(2-Methoxyphenyl)-2-(2-pyridinyl)ethanone N-oxide (20.0 g) is refluxed under nitrogen for five hours in a mixture of 48% hydrobromic acid (250 ml) and glacial acetic acid (250 ml). The reaction mixture is cooled, and the solvents are removed under reduced pressure to give a solid product. Recrystallization from absolute ethanol gives pale yellow crystals (9.7 g, 40%), m.p. dec > 230°C.

Anal. Calcd. for $C_{13}H_{10}BrNo_2$: C, 53.45; H, 3.45; N, 4.80; Br, 27.35. Found: C, 53.38; H, 3.58; N, 4.66; Br. 27.33.

EXAMPLE 2

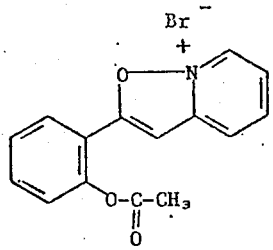

2-(2-Acetyloxyphenyl)Isoxazolo[2,3-a]Pyridinium Bromide 2-(2-Hydroxyphenyl)isoxazolo[2,3-a]pyridinium bromide from Example 1 (5.0 g) is refluxed in acetic anhydride (40 ml) under nitrogen for 60–90 minutes. The solution is cooled, and the solvent is evaporated. The oily residue is diluted with ethyl acetate to crystallize the product. Recrystallization from isopropanol gives gray-white crystals (4.16 g, 73%) m.p. 198°–201°C.

Anal. Calcd. for $C_{15}H_{12}BrNO_3$: C, 53.91; H, 3.62; N, 4.19; Br⁻, 23.91. Found: C, 53.95; H, 3,81; N, 4.18; Br⁻, 23.83.

EXAMPLE 3

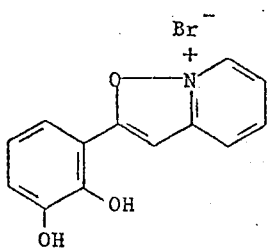

2-(2,3-Dihydroxyphenyl)Isoxazolo[2,3-a]Pyridinium Bromide

Prepared by the procedure described in Example 1, using 1-(2,3-dimethoxyphenyl)-2-(2-pyridinyl)ethanone N-oxide. Recrystallization from absolute ethanol gives pale yellow crystals (13.5g, 72%), m.p. dec > 222°C.

Anal. Calcd. for $C_{13}H_{10}BrNO_3$: C, 50.67; H, 3.27; N, 4.55; Br⁻, 25.93. Found: C, 50.50; H, 3.32; N, 4.40; Br⁻, 25.80.

EXAMPLE 4

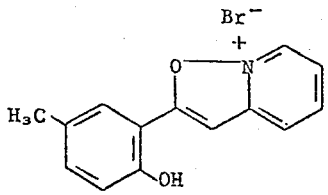

2-(2-Hydroxy-5-Methylphenyl)Isoxazolo[2,3-a]Pyridinium Bromide

Prepared by the method described in Example 1, using 1-(2-methoxy-5-methylphenyl)-2-(2-pyridinyl)ethanone N-oxide. Recrystallization from absolute ethanol gives yellow crystals (22.65 g, 47.7%), m.p. dec > 220°C.

Anal. Calcd. for $C_{14}H_{12}BrNO_2$: C, 54.92; H, 3.95; Br, 26.10; N, 4.58. Found C, 54.62; H, 4.05; Br, 25.94; N, 4.47.

EXAMPLE 5

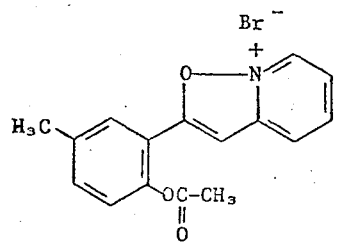

2-(2-Acetyloxy-5-Methylphenyl)Isoxazolo[2,3-a]Pyridinium Bromide

Prepared by the method described in Example 2, from 2-(2-hydroxy-5-methylphenyl)isoxazolo[2,3-a]pyridinium bromide of Example 4. Crystallized on removal of solvents. Recrystallization from absolute ethanol gives white crystls (10.48 g, 76.5%), m.p. dec > 222°C.

Anal. Calcd. for $C_{16}H_{14}BrNO_3$: C, 55.19; H, 4.05; N, 4.02; Br⁻, 22.95. Found: C, 54.92; H, 4.09; N, 4.03; Br⁻, 22.96.

EXAMPLE 6

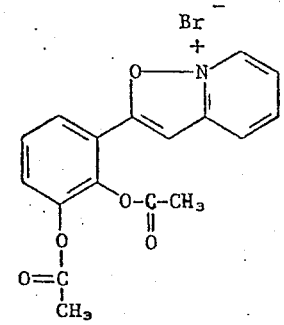

2-[2,3-Bis(Acetyloxy)Phenyl]Isoxazolo[2,3-a]Pyridinium Bromide

Prepared by the method described in Example 2 using 2-(2,3-dihydroxyphenyl)isoxazolo[2,3-a]pyridinium bromide from Example 3 (6.5 g). Crystallized on removal of solvents. Recrystallization from absolute ethanol gives light beige crystals (6.75 g, 82%), m.p. 206°–07°C.

Anal. Calcd. for $C_{17}H_{14}BrNO_5$: C, 52.06; H, 3.60; N, 3.57; Br⁻, 20.37. Found: C, 52.02; H, 3.86; N, 3.52; Br⁻, 20.33.

EXAMPLE 7

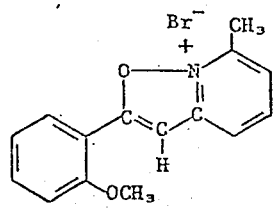

2-(Methoxyphenyl)-7-Methyl Isoxazolo[2,3-a]Pyridinium Bromide

Prepared by the method described in Example 1 using crude 1-(2-methoxyphenyl)-2-(6-methyl-2-pyridinyl)-ethanone N-oxide. Crystallized from absolute ethanol and recrystallization from same gives white crystals (1.69 g, 37.2%), m.p. dec > 220°C.

Anal. Calcd. for C₁₅H₁₄BrNO₂: C, 56.40; H, 4.38; N, 4.38; Br⁻, 25.00. Found: C, 56.05; H, 4.42; N, 4.31; Br⁻, 25.08.

EXAMPLE 8

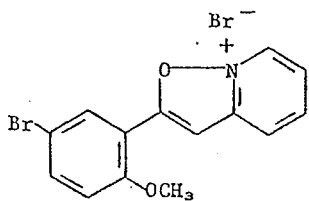

2-(2-Methoxy-5-Bromophenyl)Isoxazolo[2,3-a]Pyridinium Bromide

Prepared by the method described in Example 1 using 1-(2-methoxy-5-bromophenyl)-2-(2-pyridinyl)-ethanone N-oxide. Recrystallization from absolute ethanol gives pale yellow crystals (26.3 g; 76%), m.p. dec > 202°C.

Anal. Calcd. for C₁₄H₁₁Br₂NO₂: C, 43.56; H, 3.11; N, 3.63; Br, 41.51. Found: C, 42.29; H, 3.09; N, 3.58; Br, 40.57.

EXAMPLE 9

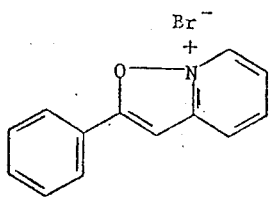

2-Phenylisoxazolo[2,3-a]Pyridinium Bromide

Prepared by the procedure described in Example 1 using 1-phenyl-2-(2-pyridinyl)ethanone N-oxide. Recrystallization from absolute ethanol gives pale yellow crystals (2.32 g, 60%), m.p. 164°–65°C.

Anal. Calcd. for C₁₃H₁₀BrNO: C, 56.55; H, 3.65; N, 5.07; Br⁻, 28.94. Found: C, 56.30; H, 3.95; N, 5.50; Br⁻, 28.88.

EXAMPLE 10

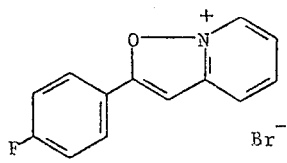

2-(4-Fluorophenyl)Isoxazolo[2,3-a]Pyridinium Bromide

Prepared by the procedure described in Example 1 using 1-(4-fluorophenyl)-2-(2-pyridinyl)ethanone N-oxide. Recrystallization twice from isopropyl alcohol gives cream-colored crystals (10.6 g, 44%), m.p. 205°–07°C.

Anal. Calcd. for C₁₃H₉BrFNO: C, 53.09; H, 3.08; N, 4.76; F, 6.46; Br, 27.17. Found: C, 51.21; H, 3.23; N, 4.55; F, 6.52; Br (total), 26.77.

Mass Spectrum observed molecular ion 295.9718 calculated for C₁₃H₉Br⁸¹FNO 295.9851

EXAMPLE 11

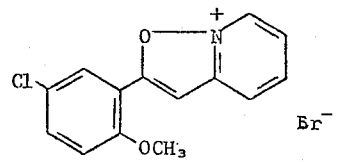

2-(5-Chloro-2-Methoxyphenyl)Isoxazolo[2,3-a]Pyridinium Bromide

Prepared by the procedure described in Example 1 using 1-(5-chloro-2-methoxyphenyl)-2-(2-pyridinyl)ethanone N-oxide. Recrystallization from isopropyl alcohol gives off-white crystals (15.5 g, 45%), m.p. 208°–210°C.

Anal. Calcd. for C₁₄H₁₁BrClNO₂: C, 49,37; H, 3.26; N, 4.11; Cl, 10.41; Br, 23.46. Found: C, 48.82; H, 3.22; N, 4.11; Cl, 10.33; Br. 23.23.

EXAMPLE 12

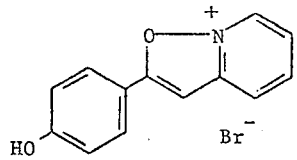

2-(4-Hydroxyphenyl)Isoxazolo[2,3-a]Pyridinium Bromide

Prepared by the method described in Example 1 using 1-(4-methoxyphenyl)-2-(2-pyridinyl)ethanone N-oxide. Recrystallization twice from absolute ethanol gives yellow crystals (19.7 g, 58.6%), m.p. dec > 180°C.

Anal. Calcd. for C₁₃H₁₀BrNO₂: C, 53.45; H, 3.45; N, 4.80; Br, 27.35. Found: C, 53.25; H, 3.53; N, 4.71; Br, 27.09.

EXAMPLE 13

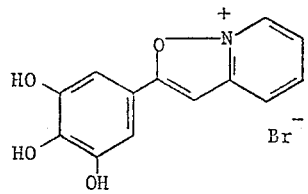

2-(3,4,5-Trihydroxyphenyl)Isoxazolo[2,3-a]Pyridinium Bromide

Prepared by the method described in Example 1 using 1-(3,4,5-trimethoxyphenyl)-2-(2-pyridinyl)ethanone N-oxide. The solid product isolated is covered by a red-brown oil. This mixture is boiled in absolute ethanol and filtered. The pale yellow-brown crystals are washed with portions of absolute ethanol and then acetone, until the wash solvent is colorless, and sucked dry (8.0 g, 33.9%), m.p. dec. > 210°C.

Anal. Calcd. for $C_{13}H_{10}BrNO_4$: C, 48.17; H, 3.11; N, 4.32; Br, 24.65. Found: C, 47.90; H, 3.18; N, 4.10; Br, 24.57.

EXAMPLE 14

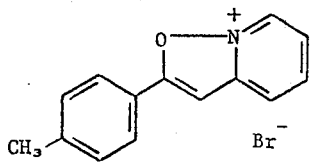

2-(4-Methylphenyl)Isoxazolo[2,3-a]Pyridinium Bromide

Prepared by the procedure described in Example 1 using 1-(4-methylphenyl)-2-(2-pyridinyl)ethanone N-oxide. Recrystallization twice from absolute ethanol gives off-white crystals (1.75 g, 16.4%), m.p. 183°-86°C.

Anal. Calcd. for $C_{14}H_{12}BrNO$: C, 57.95; H, 4.17; N, 4,83; Br, 27.54. Found: C, 56.37; H, 4.33; N, 4.47; Br, 27.08.

Mass Spectrum observed molecular ion 210.0910 calculated for $C_{14}H_{12}NO$ 210.0919

We claim:

1. A compound of the formula I:

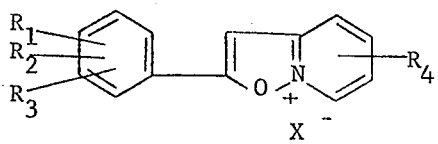

wherein $R_1$, $R_2$ and $R_3$ are each hydrogen, halogen, hydroxy, lower alkyl, lower alkoxy or lower alkanoyl; $R_4$ is hydrogen or lower alkyl; X is a bromide, chloride or iodide salt.

2. A compound according to claim 1 wherein $R_1$ is hydrogen, halogen, hydroxy, methyl, methoxy or acetoxy; $R_2$ is hydrogen, hydroxy, methyl, methoxy or acetoxy; $R_3$ is hydrogen or hydroxy; $R_4$ is hydrogen or methyl; and X is the bromide salt.

3. A compound according to claim 1 which is 2-(2-hydroxyphenyl)isoxazolo[2,3-a]pyridinium bromide.

4. A compound according to claim 1 which is 2-(2-acetyloxyphenyl)isoxazolo[2,3-a]pyridinium bromide.

5. A compound according to claim 1 which is 2-(2,3-dihydroxyphenyl)isoxazolo[2,3-a]pyridinium bromide.

6. A compound according to claim 1 which is 2-(2-hydroxy-5-methylphenyl)isoxazolo[2,3-a]pyridinium bromide.

7. A compound according to claim 1 which is 2-(2-acetyloxy-5-methylphenyl)isoxazolo[2,3-a]pyridinium bromide.

8. A compound according to claim 1 which is 2-[2,3-bis(acetyloxy)phenyl]isoxazolo[2,3-a]pyridinium bromide.

9. A compound according to claim 1 which is 2-(2-methoxyphenyl)-7-methyl isoxazolo[2,3-a]pyridinium bromide.

10. A compound according to claim 1 which is 2-(2-methoxy-5-bromophenyl)isoxazolo[2,3-a]pyridinium bromide.

11. A compound according to claim 1 which is 2-phenyl-isoxazolo[2,3-a]pyridinium bromide.

12. A compound according to claim 1 which is 2-(4-fluorophenyl)isoxazolo[2,3-a]pyridinium bromide.

13. A compound according to claim 1 which is 2-(5-chloro-2-methoxyphenyl)isoxazolo[2,3-a]pyridinium bromide.

14. A compound according to claim 1 which is 2-(4-hydroxyphenyl)isoxazolo[2,3-a]pyridinium bromide.

15. A compound according to claim 1 which is 2-(3,4,5-trihydroxyphenyl)isoxazolo[2,3-a]pyridinium bromide.

16. A compound according to claim 1 which is 2-(4-methylphenyl)isoxazolo[2,3-a]pyridinium bromide.

17. A method for treating hyperacidity in mammals which comprises the administration of a sufficient amount of a compound having the formula I:

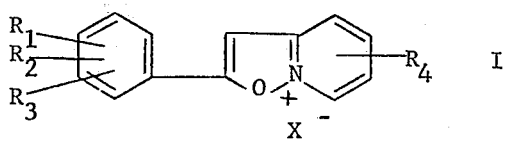

wherein $R_1$, $R_2$ and $R_3$ are each hydrogen, halogen, hydroxy, lower alkyl, lower alkoxy or lower alkanoyl; $R_4$ is hydrogen or lower alkyl; X is a bromide, chloride or iodide salt.

18. A method according to claim 17 wherein 2-(2-hydroxy-5-methylphenyl)isoxazolo[2,3-a]pyridinium bromide is administered.

19. A method for treating inflammatory conditions in mammals which comprises the administration of an anti-inflammatory amount of a compound having the formula I:

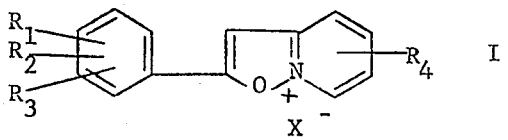

wherein $R_1$, $R_2$ and $R_3$ are each hydrogen, halogen, hydroxy, lower alkyl, lower alkoxy or lower alkanoyl; $R_4$ is hydrogen or lower alkyl; X is a bromide, chloride or iodide salt.

20. A method according to claim 19 wherein 2-(2-methoxyphenyl)-7-methylisoxazolo[2,3-a]pyridinium bromide is administered.

* * * * *